(12) United States Patent
Cornyn et al.

(10) Patent No.: US 11,766,477 B2
(45) Date of Patent: Sep. 26, 2023

(54) METHODS FOR MAKING MIXED ALLERGEN COMPOSITIONS

(71) Applicant: SOCIÉTÉ DES PRODUITS NESTLÉ S.A., Vevey (CH)

(72) Inventors: Christopher Cornyn, Woodside, CA (US); Olivia M. Weihe, Redwood City, CA (US)

(73) Assignee: Societe des Produits Nestle S.A., Vevey (CH)

( * ) Notice: Subject to any disclaimer, the term of this patent is extended or adjusted under 35 U.S.C. 154(b) by 532 days.

(21) Appl. No.: 16/750,522

(22) Filed: Jan. 23, 2020

(65) Prior Publication Data

US 2020/0230232 A1     Jul. 23, 2020

Related U.S. Application Data

(60) Provisional application No. 62/865,473, filed on Jun. 24, 2019, provisional application No. 62/795,877, filed on Jan. 23, 2019.

(51) Int. Cl.
*A61K 39/35* (2006.01)
*A61K 35/745* (2015.01)
*A61K 35/747* (2015.01)

(52) U.S. Cl.
CPC ............ *A61K 39/35* (2013.01); *A61K 35/745* (2013.01); *A61K 35/747* (2013.01)

(58) Field of Classification Search
None
See application file for complete search history.

(56) References Cited

U.S. PATENT DOCUMENTS

| | | | |
|---|---|---|---|
| 3,627,543 A | 12/1971 | Epstein | |
| 4,031,199 A | 6/1977 | Nieschulz et al. | |
| 5,520,950 A | 5/1996 | Rosenplenter | |
| 6,986,912 B2 | 1/2006 | Kramer | |
| 7,048,928 B2 | 5/2006 | Loria et al. | |
| 7,595,081 B1 | 9/2009 | Bellar | |
| 8,524,242 B2 | 9/2013 | Saito et al. | |
| 8,632,831 B2 | 1/2014 | Perry et al. | |
| 8,652,485 B2 | 2/2014 | Hafner et al. | |
| 8,802,056 B2 | 8/2014 | Shea | |
| 9,198,869 B2 | 12/2015 | Walser et al. | |
| 9,271,899 B2 | 3/2016 | Francois | |
| 9,273,129 B2 | 3/2016 | Simon | |
| 9,345,761 B2 | 5/2016 | Esch | |
| 9,402,896 B2 | 8/2016 | Tang | |
| 9,481,716 B2 | 11/2016 | Clark et al. | |
| 9,526,781 B2 | 12/2016 | Koppelman et al. | |
| 9,539,318 B2 | 1/2017 | Dupont et al. | |
| 9,724,271 B2* | 8/2017 | Francois ............... | A61K 39/36 |
| 9,731,003 B2 | 8/2017 | Nadeau | |
| 9,744,230 B2 | 8/2017 | Hearl et al. | |
| 9,808,517 B2 | 11/2017 | Putnam et al. | |
| 10,064,936 B2 | 9/2018 | Nadeau | |
| 10,143,742 B2 | 12/2018 | Nadeau | |
| 10,149,904 B2 | 12/2018 | Nadeau | |
| 10,166,286 B2 | 1/2019 | Nadeau | |
| 10,525,124 B2 | 1/2020 | Nadeau | |
| 10,525,125 B2 | 1/2020 | Nadeau | |
| 10,695,422 B2 | 6/2020 | Nadeau | |
| 11,007,264 B2 | 5/2021 | Nadeau | |
| 11,147,871 B2 | 10/2021 | Nadeau | |
| 11,278,615 B2 | 3/2022 | Nadeau | |
| 11,382,934 B2 | 7/2022 | Dombkowski et al. | |
| 2004/0000543 A1 | 1/2004 | Dudek et al. | |
| 2005/0025862 A1 | 2/2005 | Morad et al. | |
| 2007/0202211 A1 | 8/2007 | Altom et al. | |
| 2009/0324650 A1 | 12/2009 | Legon et al. | |
| 2010/0041808 A1 | 2/2010 | Canfer et al. | |
| 2010/0278880 A1 | 11/2010 | Legon et al. | |
| 2011/0229523 A1 | 9/2011 | Koppelman et al. | |
| 2012/0207815 A1 | 8/2012 | Benhamou et al. | |
| 2013/0108706 A1 | 5/2013 | Svennevig | |
| 2013/0218132 A1 | 8/2013 | Francois | |
| 2013/0302374 A1 | 11/2013 | Esch | |
| 2014/0010845 A1 | 1/2014 | Brimnes et al. | |
| 2014/0023757 A1 | 1/2014 | Christensen | |
| 2014/0027445 A1 | 1/2014 | Scheurs et al. | |
| 2014/0271721 A1 | 9/2014 | Walser et al. | |
| 2014/0335259 A1 | 11/2014 | Vurma et al. | |
| 2015/0050301 A1 | 2/2015 | Kettner et al. | |
| 2015/0150956 A1 | 6/2015 | Henot et al. | |
| 2015/0343075 A1 | 12/2015 | Raff | |
| 2016/0030553 A1 | 2/2016 | Legon | |
| 2016/0051593 A1 | 2/2016 | Raff | |
| 2016/0051639 A1 | 2/2016 | Raff | |

(Continued)

FOREIGN PATENT DOCUMENTS

| CN | 101646418 | 2/2010 |
|---|---|---|
| CN | 102048077 A | 5/2011 |

(Continued)

OTHER PUBLICATIONS

Rappaport, B. The Allergic Activity of Proteins Sterilized by Dry Heat. The Journal of Allergy 4(1)1-8, 1932. (Year: 1932).*
American Thoracic Society (2016) "Early introduction of allergenic foods reduces risk of food sensitization," (1 page).
Begin et al. (2014) "Phase 1 results of safety and tolerability in a rush oral immunotherapy protocol to multiple foods using Omalizumab," Allergy Asthma Clin. Immunol., 10(1): 7 (10 pages).
Begin et al. (2014) "Safety and feasibility of oral immunotherapy to multiple allergens for food allergy," Allergy Asthma Clin. Immunol., 10(1): 1 (8 pages).
Begin et al. (2016) "Erratum to: Safety and feasibility of oral immunotherapy to multiple allergens for food allergy," Allergy Asthma Clin. Immunol., 12: 28 (1 page).

(Continued)

*Primary Examiner* — Michael Barker
(74) *Attorney, Agent, or Firm* — K&L Gates LLP

(57) ABSTRACT

Methods of making mixed allergen products are provided, wherein the mixed allergen products are substantially free of replication viable organisms.

23 Claims, 5 Drawing Sheets

(56) References Cited

U.S. PATENT DOCUMENTS

| | | |
|---|---|---|
| 2016/0206731 A1 | 7/2016 | Francois |
| 2016/0228539 A1 | 8/2016 | Nelson et al. |
| 2016/0235109 A1 | 8/2016 | Cavestro et al. |
| 2016/0263212 A1 | 9/2016 | Friedman et al. |
| 2016/0324955 A1 | 11/2016 | Benhamou et al. |
| 2016/0330998 A1 | 11/2016 | Jimenez-Marquez et al. |
| 2016/0331834 A1 | 11/2016 | Mondoulet et al. |
| 2017/0100476 A1 | 4/2017 | Legon et al. |
| 2017/0151325 A1 | 6/2017 | Benhamou et al. |
| 2017/0304432 A1 | 10/2017 | Hearl et al. |
| 2017/0333386 A1 | 11/2017 | Lila et al. |
| 2017/0360922 A1 | 12/2017 | Turke |
| 2018/0020712 A1 | 1/2018 | Brown |
| 2018/0177895 A1 | 6/2018 | Mills et al. |
| 2018/0200361 A1 | 7/2018 | Simon et al. |
| 2019/0038741 A1 | 2/2019 | Nadeau |
| 2019/0269774 A1 | 9/2019 | Dombkowski et al. |
| 2019/0365885 A1 | 12/2019 | Nadeau |
| 2020/0155615 A1 | 5/2020 | Dombkowski et al. |
| 2020/0171145 A1 | 6/2020 | Nadeau |
| 2022/0016238 A1 | 1/2022 | Weihe et al. |
| 2022/0080041 A1 | 3/2022 | Nadeau |
| 2022/0133882 A1 | 5/2022 | Nadeau |
| 2022/0241404 A1 | 8/2022 | Nadeau |

FOREIGN PATENT DOCUMENTS

| | | |
|---|---|---|
| CN | 102596237 | 7/2012 |
| CN | 102695427 | 9/2012 |
| CN | 102 986 802 A | 3/2013 |
| CN | 104273238 A | 1/2015 |
| EP | 0155760 A1 | 9/1985 |
| WO | WO-2001040264 | 6/2001 |
| WO | WO-2008043157 A1 | 4/2008 |
| WO | WO-2013078510 A1 | 6/2013 |
| WO | WO-2015042402 A1 | 3/2015 |
| WO | WO-2015185684 A1 | 12/2015 |
| WO | WO-2016020336 A1 | 2/2016 |
| WO | WO-2016134291 A2 | 8/2016 |
| WO | WO-2017048860 A1 | 3/2017 |
| WO | WO-2017139558 A1 | 8/2017 |
| WO | WO-2018065538 A1 | 4/2018 |
| WO | WO-2018093932 A2 | 5/2018 |
| WO | WO-2018094390 A1 | 5/2018 |
| WO | WO-2018112553 A1 | 6/2018 |
| WO | WO-2019018529 A1 | 1/2019 |
| WO | WO-2020113060 A1 | 6/2020 |
| WO | WO-2020154476 A1 | 7/2020 |

OTHER PUBLICATIONS

Bunyavanich et al. (2014) "Peanut, milk, and wheat intake during pregnancy is associated with reduced allergy and asthma in children," J. Allergy Clin. Immunol., 133(5): 1373-82.
Chinthrajah et al. (2016) "Molecular and cellular mechanisms of food allergy and food tolerance," J. Allergy Clin. Immunol., 137(4):984-97.
Choi et al. (2007) "Consumer-Based Optimization of a Third-Generation Product Made from Peanut and Rice Flour," Journal of Food Science, 72(7): S443-S449.
Cuello-Garcia et al. (2015) "Probiotics for the prevention of allergy: A systematic review and meta-analysis of randomized controlled trials," J. Allergy Clin. Immunol., 136(4):952-61.
Du Toit et al. (2008) "Early consumption of peanuts in infancy is associated with a low prevalence of peanut allergy," J. Allergy Clin. Immunol., 122(5): 984-991.
Du Toit et al. (2015) "Randomized Trial of Peanut Consumption in Infants at Risk for Peanut Allergy," N. Engl. J. Med., 372(9):803-13.
Du Toit et al. (2016) "Effect of Avoidance on Peanut Allergy after Early Peanut Consumption," N. Engl. J. Med., 374(15):1435-43.
Du Toit et al. (2016) "Prevention of food allergy," J. Allergy Clin. Immunol., 137(4):998-1010.
Dyer et al. (2015) "Epidemiology of childhood peanut allergy," Allergy Asthma Proc., 36(1):58-64.
Egg Nutritional Information. https://en.wikipedia.org/wiki/Egg_as_food.
Extended European Search Report for European Application No. 16753171.4, dated Jun. 11, 2018 (8 pages).
Favorite Brand Name Recipe Cookbook. Beekman House, New York 1991, pp. 290 and 296 (Cherry Winks and Shredded Wheat Cookies).
Feeney et al. (2016) "Impact of peanut consumption in the LEAP Study: Feasibility, growth, and nutrition," J. Allergy Clin. Immunol., 138(4):1108-1118.
Frazier et al. (2013) "Prospective Study of Peripregnancy Consumption of Peanuts or Tree Nuts by Mothers and the Risk of Peanut or Tree Nut Allergy in Their Offspring," JAMA Pediatr., 168(2):156-162.
Gupta et al. (2011) "The prevalence, severity, and distribution of childhood food allergy in the United States," Pediatrics. 128(1):e9-17.
Gupta et al. (2013) "Factors associated with reported food allergy tolerance among US children," Ann. Allergy Asthma Immunol., 111(3):194-198.
Gupta et al. (2013) "The economic impact of childhood food allergy in the United States," JAMA Pediatr., 167(11):1026-31.
Howard et al. (2010) "Analysis of Ingredient Functionality and Formulation Optimization of an Instant Peanut Beverage Mix," Journal of Food Science, 75(1): S8-S19.
Howard et al. (2011) "Analysis of Ingredient Functionality and Formulation Optimization of Pasta Supplemented with Peanut Flour" Journal of Food Science, 76(1): E40-E47.
http://allergen.org/search.php?allergensource=peanut&searchsource=Search.
International Search Report for PCT/US2016/018731, dated Aug. 22, 2016 (5 pages).
International Search Report for PCT/US2018/042696, dated Sep. 24, 2018 (5 pages).
Kando et al. (2011) "Oral Immunotherapy to the Food-allergic children," Bulletin of Japanese Pediatrics, No. 41, éÉ.91-94.
Katz et al. (2010) "Early exposure to cow's milk protein is protective against IgE-mediated cow's milk protein allergy," J. Allergy Clin. Immunol., 126(1):77-82.
Kim et al. (2016) "Dietary antigens limit mucosal immunity by inducing regulatory T cells in the small intestine," Science, 351(6275):858-63.
Koplin et al. (2010) "Can early introduction of egg prevent egg allergy in infants? A population-based study," J. Allergy Clin. Immunol., 126(4):807-13.
Koplin et al. (2016) "Understanding the feasibility and implications of implementing early peanut introduction for prevention of peanut allergy," J. Allergy Clin. Immunol., 138(4):1131-1141.
Kristensen et al. (2016) "Alterations in fecal microbiota composition by probiotic supplementation in healthy adults: a systematic review of randomized controlled trials," Genome Med., 8(1):52.
Kristiansen et al. "Allergen immunotherapy for the prevention of allergy: A systematic review and meta-analysis." Pediatr Allergy Immunol. Feb. 2017;28(1 ): 18-29. doi: 10.1111/pai .12661. Epub Dec. 12, 2016.
Kull et al. (2006) "Fish consumption during the first year of life and development of allergic diseases during childhood," Allergy, 61: 1009-1015.
Lau et al. (2012) "Parent report of childhood shellfish allergy in the United States," Allergy Asthma Proc., 33(6):474-80.
Martignago et al. "Preventive actions of allergen immunotherapy: the facts and the effects in search of evidence." Clin Mol. Allergy 2017; 15: 13. Published online Jun. 15, 2017. doi: 10.1186/s12948-017-0070-7.
Mosha et al. (2004) "Nutritional value and acceptability of homemade maize/sorghum-based weaning mixtures supplemented with rojo bean flour, ground sardines and peanut paste," International Journal of Food Sciences and Nutrition, 55(4): 301-315.
Nwaru et al. (2010) "Age at the Introduction of Solid Foods During the First Year and Allergic Sensitization at Age 5 Years," Pediatrics, 125(1):50-9.

(56) References Cited

OTHER PUBLICATIONS

Nwaru et al. (2013) "Timing of infant feeding in relation to childhood asthma and allergic diseases," J. Allergy Clin. Immunol., 131(1): 78-86.
Otani et al. (2014) "Multiple-allergen oral immunotherapy improves quality of life in caregivers of food-allergic pediatric subjects," Allergy Asthma Clin. Immunol., 10(1):25 (7 pages).
Ozdemir (2010) "Various effects of different probiotic strains in allergic disorders: an update from laboratory and clinical data," Clin. Exp. Immunol., 160(3):295-304.
Pali-Sholl et al., J. Allergy Clin. Immunol., 2009, vol. 123, No. 5, pp. 1012-1021.
Perkin et al. (2016) "Randomized Trial of Introduction of Allergenic Foods in Breast-Fed Infants," N. Engl. J. Med., 374(18):1733-43.
Prinyawiwatkul et al. (1993) "Optimization of Sensory Qualities of an Extruded Snack Based on Cornstarch and Peanut Flour," Lebensm.-Wiss. u.—Technol. (26(5): 393-399.
Reilly et al. (2016) "The Gluten-Free Diet: Recognizing Fact, Fiction, and Fad," J. Pediatr., 175:206-10.
Reisacher, et al. (2016) "Oral mucosal immunotherapy for allergic rhinitis: A pilot study," Allergy Rhinol., 7(1):21-8.
Rudders et al. (2015) "Sunlight, vitamin D and food allergy," Curr. Opin. Allergy Clin. Immunol., 15(4):350-7.
Ryan et al. (2016) "Successful immunotherapy induces previously unidentified allergen-specific CD4+ T-cell subsets," Proc. Natl. Acad. Sci. U.S.A., 113(9):E1286-95.
Shaikh et al. (1993) "A retrospective study on the safety of immunotherapy in pregnancy," Clin. Exp. Allerg. 23(10): 857-860.
Shredded wheat nutritional information, 2017.
Syed et al. (2014) "Peanut oral immunotherapy results in increased antigen-induced regulatory T-cell function and hypomethylation of forkhead box protein 3 (FOXP3)," J. Allergy Clin. Immunol., 133(2):500-10.
Takagi et al. (2005) "A rice-based edible vaccine expressing multiple T cell epitopes including oral tolerance for inhibition of Th2-mediated IgE responses," PNAS, 102(48): 17525-17530.
The Journal of Pediatrics (2016) "The Gluten-Free Diet in Children: Do the Risks Outweigh the Benefits?" (2 pages).
Tran et al. (2016) "The Effects of Infant Feeding Practices on Food Sensitization in a Canadian Birth Cohort," American Thoracic Society 2016 International Conference, Session: D31 Novel Mechanisms of Allergy and Airway Inflammation, Abstract 8568 (2 pages).
Walnut Nutritional Information. https://en.wikipedia.org/wiki/Walnut.
Warren et al. (2013) "The epidemiology of milk allergy in US children," Ann. Allergy Asthma Immunol., 110(5):370-4.
Weinstock (2016) "A Glimpse of Microbial Power in Preventive Medicine," JAMA Pediatr. 170(1):11.
Written Opinion for PCT/US2016/018731, dated Aug. 2, 2016 (6 pages).
Written Opinion for PCT/US2018/042696, dated Sep. 24, 2018 (12 pages).
Zolkipli et al. (2015) "Randomized controlled trial of primary prevention of atopy using house dust mite allergen oral immunotherapy in early childhood," J. Allergy Clin. Immunol., 136(6):1541-7.
Baron et al. (2003) "Effect of dry heating on the microbiological quality, functional properties, and natural bacteriostatic ability of egg white after reconstitution," J. Food Prot., 66(5): 825-32.
International Search Report for PCT/US2017/062781, dated Mar. 6, 2018 (3 pages).
International Search Report for PCT/US2019/063686, dated Mar. 20, 2020 (6 pages).
International Search Report for PCT/US2020/014748, dated May 15, 2020 (4 pages).
Kaddouri et al. (2008) "Impact of Gamma-radiation on antigenic properties of cow's milk Beta-Lactoglobulin," J. Food Prot., 71(6): 1270-1272.
Moriyama et al. (2013) "Effect of Gamma Irradiation on Soybean Allergen Levels," Biosci. Biotechnol. Biochem., 77(12): 2371-2377.
Veber et al. (1994) "Sterilisation by radiation of allergen raw materials," J. Allergy Clin. Immunol., 93(1), Abstract 173, p. 191.
Written Opinion for PCT/US2017/062781, dated Mar. 6, 2018 (8 pages).
Written Opinion for PCT/US2019/063686, dated Mar. 20, 2020 (8 pages).
Written Opinion for PCT/US2020/014748, dated May 15, 2020 (7 pages).

\* cited by examiner

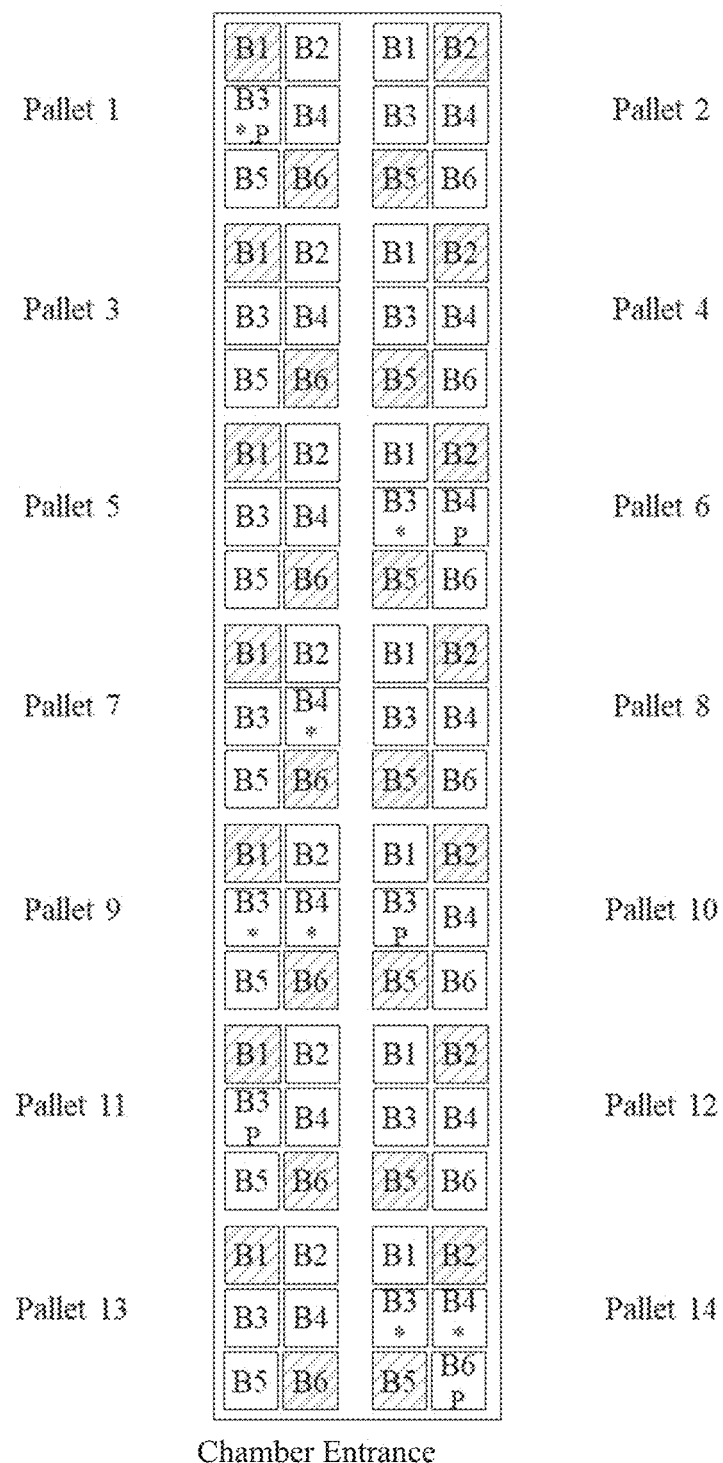

METHODS FOR MAKING MIXED ALLERGEN COMPOSITIONS

CROSS-REFERENCE TO RELATED APPLICATIONS

This application claims the benefit of and priority to U.S. Provisional Patent Application No. 62/795,877, filed Jan. 23, 2019, and to U.S. Provisional Patent Application No. 62/865,473, filed Jun. 24, 2019, the disclosure of which is hereby incorporated by reference in its entirety for all purposes.

BACKGROUND

Allergy is a disorder of the immune system characterized by the occurrence of allergic reactions to normally harmless environmental substances. Allergies are caused by allergens, which may be present in a wide variety of sources including, but not limited to, pollens or other plant components, dust, molds or fungi, foods, additives, latex, transfusions, animal or bird danders, insect venoms, radiocontrast medium, medications, or chemicals. Common allergic reactions include eczema, hives, hay fever, asthma, and reactions to venoms. Mild allergies, like hay fever, are highly prevalent in the human population and cause symptoms such as allergic conjunctivitis, itchiness, and runny nose. In some people, severe allergies to environmental allergens, dietary allergens, or medication may result in life-threatening anaphylactic reactions if left untreated.

A food allergy is an adverse immune response to a food allergen, for example, a food protein. Common food allergens are found in shellfish, peanuts, tree nuts, fish, milk, eggs, soy and fresh fruits such as strawberries, mangoes, bananas, and apples. Immunoglobulin E (IgE)-mediated food allergies are classified as type-I immediate hypersensitivity reactions. These allergic reactions have an acute onset (from seconds to one hour) and the accompanying symptoms may include: angioedema (soft tissue swelling of the eyelids, face, lips, tongue, larynx and trachea); hives; itching of the mouth, throat, eyes, and skin; gastrointestinal symptoms such as nausea, vomiting, diarrhea, stomach cramps, and abdominal pain; rhinorrhea or nasal congestion; wheezing; shortness of breath; difficulty swallowing; and anaphylaxis, a severe, whole-body allergic reaction that can result in death. It is estimated that 1 out of 12 children under 21 years of age have a diagnosed food allergy, and over $24 billion is spent per year on health care costs for food allergic reactions, largely due to about 90,000 emergency room visits per year in the U.S. alone due to food-induced anaphylaxis. Moreover, deaths occur every year due to fatal food allergies.

Accordingly, there exists a need in the art for allergen compositions that can prevent and/or treat allergies, and methods for making allergen compositions to prevent and/or treat allergies.

SUMMARY

This disclosure is directed, at least in part, to a method of making a mixed allergen product substantially free of replication viable organisms. For example, in certain embodiments, the method comprises: providing bulk mixed allergen material comprising 2 to 20 individual complete food allergens; and sterilizing the bulk mixed allergen material by dry heat sterilization, thereby obtaining the mixed allergen product.

In certain embodiments, a method further comprises providing 2 to 20 individual complete food allergens and blending the 2 to 20 individual complete food allergens together to obtain the bulk mixed allergen material.

In other embodiments, the disclosure provides a method, wherein the 2 to 20 individual complete food allergens are selected from the group consisting of almond, cashew, cod, egg, hazelnut, milk, oat, peanut, pecan, pistachio, salmon, sesame, shrimp, soy, walnut, and wheat.

In another embodiment, the disclosure provides a method, wherein the blending further comprises blending the 2 to 20 individual complete food allergens with one or more than one bulking agent.

In certain embodiments of the present disclosure, blending comprises loading 2 to 20 individual complete food allergens into a ribbon blender set at about 10 Hz to about 50 Hz for about 10 minutes to about 50 minutes. In other embodiments, the bulk mixed allergen material is discharged into lined drums after blending.

In certain embodiments, a method of the present disclosure further comprises filtering the mixed allergen product. In some embodiments, filtering comprises passing the mixed allergen product through a screen ranging from a #5 mesh (US) screen to a #10 mesh (US) screen on a shaker for about 1 minute to about 10 minutes.

In some embodiments, a method of the present disclosure further comprises passing the mixed allergen product through a rare earth magnet, metal detector, and metal separator.

In certain embodiments, a described method of the present disclosure provides applying dry heat sterilization, wherein the dry heat sterilization is at a temperature of about 65° C. to about 175° C. for about 18 hours to about 72 hours. In some embodiments, the dry heat sterilization comprises using a sterilization system having a furnace and a heating chamber, wherein the furnace provides about 250,000 BTUs to about 750,000 BTUs of heat to the heating chamber. In certain embodiments, the bulk mixed allergen material is first packaged into thermoresistant packaging before dry heat sterilization. In certain embodiments, temperature probes are placed with the bulk mixed allergen material during sterilizing to monitor the temperature of the dry heat sterilization.

In certain embodiments of the present disclosure, the mixed allergen product has at least about a 1 log reduction to at least about a 4 log reduction in aerobic bacterial organism plate counts as compared to corresponding bulk mixed allergen material that has not been sterilized. In some embodiments, the mixed allergen product has less than about 10,000 CFU/g of aerobic bacterial organisms. In other embodiments, the mixed allergen product has less than about 10 CFU/g of coliforms, *Escherichia coli, Enterobacteriaceae*, mold, *Staphylococcus aureus*, and yeast. In certain embodiments, the mixed allergen product has less than about 10 CFU/g of *Salmonella*. In certain embodiments, the mixed allergen product has less than about 10 CFU/g of *Cronobacter*. In further embodiments, the mixed allergen product is negative in PCR-based assays for *Listeria* species, *Cronobacter* species and *Salmonella* species per 25 g of mixed allergen product, 25 g of mixed allergen product, and 375 g of mixed allergen product, respectively.

In some embodiments of the present disclosure, the mixed allergen product has a fat content of about 10% to about 20% by weight.

In other embodiments, protein integrity of the mixed allergen product is substantially similar to protein integrity of corresponding bulk mixed allergen material that has not been sterilized. In some embodiments, the protein integrity of the mixed allergen product is determined by SDS-PAGE.

In certain embodiments, the mixed allergen product has a protein content of about 40% to about 50% by weight.

In certain embodiments, the mixed allergen product has about 1% to about 10% moisture by weight. In other embodiments, the mixed allergen product has a water activity of about 0.1 to about 0.6.

In certain embodiments of the present disclosure, the mixed allergen product comprises less than about 10% by weight of particles having a diameter greater than 500 µm.

In some embodiments, the mixed allergen product is darker in color as compared to corresponding bulk mixed allergen material that has not been sterilized. In other embodiments, the mixed allergen product has a substantially similar taste profile as compared to corresponding bulk mixed allergen material that has not been sterilized.

In certain embodiments, a described method of the present disclosure comprises one or more than one further application of dry heat sterilization.

In an alternative embodiment, the present disclosure describes a method of making a mixed allergen product substantially free of replication viable organisms, comprising: providing 2 to 20 individual complete food allergens; sterilizing each of the 2 to 20 individual complete food allergens by dry heat sterilization, thereby obtaining 2 to 20 sterilized individual complete food allergens; and blending the 2 to 20 sterilized individual complete food allergens together, thereby obtaining the mixed allergen product.

In another embodiment, the present disclosure describes a method of making a mixed allergen product substantially free of replication viable organisms, wherein the method further comprises blending the mixed allergen product with one or more than one probiotic selected from the group consisting of *Lactobacillus rhamnosus, Anaerostipes caccae*, and *Bifidobactierium longum*.

In yet another embodiment, the mixed allergen product is further blended with one or more than one prebiotic, for example, wherein the prebiotic is fructooligosaccharide.

Also disclosed is a mixed allergen product substantially free of replication viable organisms prepared by any one of the methods disclosed herein.

BRIEF DESCRIPTION OF THE DRAWINGS

FIG. 2B is a schematic showing the placement of pallets and sample boxes containing thermoresistant bags of bulk mixed allergen material in a dry heat sterilization chamber for validation trial 2. B3 of pallets 5 and 14 have chamber probes placed inside the boxes for temperature monitoring. B4 of pallets 4 and 8 have chamber probes placed inside the boxes, and B4 of pallets 6 and 9 have chamber probes placed outside the boxes. Shaded boxes indicate empty boxes without thermoresistant bags containing bulk mixed allergen material. Asterisks ("*") indicate boxes having two thermoresistant bags containing bulk mixed allergen material. "P" indicates boxes having a MadgeTech probe.

DETAILED DESCRIPTION

Figure 1:
FIG. 1 is a macroscopic image of non-sterilized bulk mixed allergen material sample and bulk mixed allergen material samples which have been heated in a laboratory oven for 5 minutes at 95° C., 105° C., 110° C., or 120° C.

Disclosed herein are methods of making a mixed allergen product substantially free of replication viable organisms.

By "replication viable organisms", it is meant organisms that are capable of multiplying, reproducing, propagating, and/or producing colony forming units (CFU) on a plate culture.

By "sterilization", it is meant a process that is capable of substantially reducing the number of replication viable organisms.

As used herein, an "individual complete food allergen" refers to a food substance containing all possible antigenic components for said food substance (for example, allergenic proteins). Individual complete food allergens may include, but are not limited to, unprocessed or processed food substances, concentrated food substances, and isolated food substances.

"Allergenic proteins", as used herein, are antigenic components of food allergens that are, either directly or indirectly, responsible for eliciting a biological allergic response. Allergenic proteins may include, but are not limited to, nut proteins such as hazelnut proteins (e.g., Cor a 1, Cor a 2, Cor a 6, Cor a 8, Cor a 9, Cor a 10, Cor a 11, Cor a 12, Cor a 13, and Cor a 14), cashew proteins (e.g., Ana o 1, Ana o 2, and Ana o 3), pistachio proteins (e.g., Pis v 1, Pis v 2, Pis v 3, Pis v 4, and Pis v 5), walnut proteins (e.g., Jug r 1, Jug r 2, Jug r 3, Jug r 4, Jug r 5, Jug r 6, Jug r 7, and Jug r 8, Jug n1, Jug n 2, and Jug n 4), pecan proteins (e.g., Car i 1, Car i 2, and Car i 4), almond proteins (e.g., Pru du 3, Pru du 4, Pru du 5, Pru du 6, and Pru du 8), peanut proteins (e.g., Ara h 1, Ara h 2, Ara h 3, Ara h 4, Ara h 5, Ara h 6, Ara h 7, Ara h 8, Ara h 9, Ara h 10, Ara h 11, Ara h 12, Ara h 13, Ara h 14, Ara h 15, Ara h 16, and Ara h 17), and brazil nut proteins (e.g., Ber e 1 and Ber e 2). Allergenic proteins may also include, but are not limited to, animal proteins such as egg proteins (e.g., Gal d 1, Gal d 2, Gal d 3, Gal d 4, Gal d 5, Gal d 6, Gal d 7, Gal d 8, Gal d 9, Gal d 10), milk proteins (e.g., Bos d 2, Bos d 3, Bos d 4, Bos d 5, Bos d, 6, Bos d 7, Bos d 8, Bos d 9, Bos d 10, Bos d 11, and Bos d 12), salmon proteins (e.g., Onc k 5, Sal s 1, Sal s 2, and Sal s 3), cod proteins (e.g., pGad c 1, Gad m 1, Gad m 2, and Gad m 3), shrimp proteins (e.g., Cra c 1, Cra c 2, Cra c 4, Cra c 5, Cra c 6, Cra c 8, Lit v 1, Lit v 2, Lig v 3, Lit v 4, Met e 1, Pan b 1, Pen a 1, Pen i 1, Pen m 1, Pen m 2, Pen m 3, Pen m 4, and Pen m 6), and crab proteins (e.g., Cha f 1, Por p1, Scy p 2, Scy p 4, and Scy p 8). Allergenic proteins may further include, but are not limited to, non-nut plant proteins such as wheat proteins (e.g., Tri a 12, Tri a 14, Tri a 15, Tri a 17, Tri a 18, Tri a 19, Tri a 20, Tri a 21, Tri a 25, Tri a 26, Tri a 27, Tri a 28, Tri a 29, Tri a 30, Tri a 31, Tri a 32, Tri a 33, Tri a 34, Tri a 35, Tri a 36, Tri a 37, Tri a 39, Tri a 40, Tri a 41, Tri a 42, Tri a 43, Tri a 44, and Tri a 45), soy proteins (e.g., Gly m 1, Gly m 1.0101, Gly m 2, Gly m 3, Gly m 4, Gly m 5, Gly m 6, Gly m 7, and Gly m 8), chickpea proteins, sesame seed proteins (e.g., Ses i 1, Ses i 2, Ses i 3, Ses i 4, Ses i 5, Ses i 6, and Ses i 7), kiwi proteins (e.g., Act c 1, Act c 5, Act c 8, Act c 10, Act d 1, Act d 2, Act d 3, Act d 4, Act d 5, Act d 6, Act d 7, Act d 8, Act d 9, Act d 10, Act d 11, Act d 12, and Act d 13), carrot proteins (e.g., Dau c 1, Dau c4, and Dau c5), celery proteins (e.g., Api q 1, Api q 2, Api q 3, Api q 4, Api q 5, and Api q 6), stone fruit proteins (e.g., Pru ar 1, Pru ar 3, Pru av 1, Pru av 2, Pru av 3, Pru av 4, Pru p 1, Pru p 2, Pru p 3, Pru p4, Pru p 7, and Pru d 3), and oat proteins.

Presently disclosed, for example, is a method of making a mixed allergen product substantially free of replication viable organisms, comprising: providing bulk mixed allergen material comprising 2 to 20 individual complete food allergens; and sterilizing the bulk mixed allergen material by dry heat sterilization, thereby obtaining the mixed allergen product.

In certain embodiments, bulk mixed allergen material comprises 2 to 20 individual complete food allergens, for example, 4 to 20, 6 to 20, 8 to 20, 10 to 20, 12 to 20, 14 to 20, 16 to 20, 18 to 20, 2 to 18, 4 to 18, 6 to 18, 8 to 18, 10 to 18, 12 to 18, 14 to 18, 16 to 18, 2 to 16, 4 to 16, 6 to 16, 8 to 16, 10 to 16, 12 to 16, or 14 to 16 individual complete food allergens. For example, bulk mixed allergen material may comprise 2, 3, 4, 5, 6, 7, 8, 9, 10, 11, 12, 13, 14, 15, 16, 17, 18, 19, or 20 individual complete food allergens. In a particular embodiment, bulk mixed allergen material comprises 15 or 16 individual complete food allergens.

For example, in certain embodiments, the individual complete food allergens are selected from the group consisting of nut, seed, legume, egg, dairy, fish and crustacean. In particular embodiments, the individual complete food allergens are selected from the group consisting of almond, cashew, hazelnut, peanut, pecan, pistachio, walnut, sesame, soy, egg, milk, oat, wheat, cod, salmon, and shrimp. In certain embodiments, the individual complete food allergens are almond, cashew, hazelnut, peanut, pecan, pistachio, walnut, sesame, soy, egg, milk, oat, wheat, cod, salmon, and shrimp. It is contemplated that the individual complete food allergens may be provided as a meal, flour, powder, and/or protein concentrate.

In certain embodiments, a described method further comprises providing 2 to 20 individual complete food allergens, and blending the 2 to 20 individual complete food allergens together to obtain bulk mixed allergen material. It will be appreciated that two or more individual complete food allergens may be provided in combination prior to blending. For example, 2 to 20, 4 to 20, 6 to 20, 8 to 20, 10 to 20, 12 to 20, 14 to 20, 16 to 20, 18 to 20, 2 to 18, 4 to 18, 6 to 18, 8 to 18, 10 to 18, 12 to 18, 14 to 18, 16 to 18, 2 to 16, 4 to 16, 6 to 16, 8 to 16, 10 to 16, 12 to 16, or 14 to 16 individual complete food allergens may be provided in combination prior to blending. In a further example, 2, 3, 4, 5, 6, 7, 8, 9, 10, 11, 12, 13, 14, 15, 16, 17, 18, 19, or 20 individual complete food allergens may be provided in combination prior to blending.

It will be appreciated that blending may comprise one or more than one blending steps to obtain bulk mixed allergen material. For example, individual complete food allergens may be blended in 1 to 19, 1 to 17, 1 to 15, 1 to 13, 1 to 11, 1 to 9, 1 to 7, 1 to 5, or 1 to 3 blending steps. In a particular embodiment, blending comprises mixing individual complete food allergens in a single blending step.

As contemplated in the present disclosure, bulk mixed allergen material is sterilized by dry heat sterilization. It will be appreciated that sterilizing may further comprise one or more than one additional application of dry heat sterilization, to inactivate heat-resistant spores.

In certain embodiments, dry heat may be supplied to a treatment chamber of a sterilization system within which bulk mixed allergen material is held or is conveyed, wherein the treatment chamber may be heated to a temperature of about 65° C. to about 175° C. For example, in certain embodiments, the treatment chamber may be heated to about 65° C. to about 80° C., about 65° C. to about 120° C., about 100° C. to about 150° C., or about 125° C. to about 175° C. In particular embodiments, the treatment chamber may be heated to a temperature of about 65° C., about 66° C., about 67° C., about 68° C., about 69° C., about 70° C., about 71° C., about 72° C., about 73° C., about 74° C., about 75° C., about 85° C., about 95° C., about 105° C., about 115° C., about 125° C., about 135° C., about 145° C., about 155° C., about 165° C., or about 175° C. In further embodiments, dry heat may be applied to bulk mixed allergen material for about 3 minutes to about 72 hours. In certain embodiments, for example, dry heat may be applied for about 3 minutes to about 72 hours, about 30 minutes to about 72 hours, about 12 hours to about 72 hours, about 18 hours to about 72 hours, about 24 hours to about 72 hours, about 30 hours to about 72 hours, about 36 hours to about 72 hours, about 42 hours to about 72 hours, about 48 hours to about 72 hours, about 54 hours to about 72 hours, about 60 hours to about 72 hours, or about 66 hours to about 72 hours. For example, in particular examples, dry heat may be applied to bulk mixed allergen material for about 30 minutes, about 45 minutes, about 60 minutes, about 75 minutes, about 90 minutes, about 105 minutes, about 120 minutes, about 12 hours, about 18 hours, about 24 hours, about 30 hours, about 36 hours, about 42 hours, about 48 hours, about 54 hours, about 60 hours, about 66 hours, or about 72 hours.

In certain embodiments, for example, dry heat may be provided to a treatment chamber of a sterilization system by multiple natural gas fired furnaces that provide about 250,000 BTUs to about 750,000 BTUs of heat to the treatment chamber. For example, about 250,000 BTUs, about 300,000 BTUs, about 350,000 BTUs, about 400,000 BTUs, about 450,000 BTUs, about 500,000 BTUs, about 550,000 BTUs, about 600,000 BTUs, about 650,000 BTUs, about 700,000 BTUs, or about 750,000 BTUs of heat may be provided to the treatment chamber.

In a further embodiment, dry heat sterilization may be applied to bulk mixed allergen material packaged in thermoresistant packaging. As used herein, "thermoresistant" is understood to mean that applying the same temperature and duration of heat to the packaging material as concurrently applied to the bulk mixed allergen material packaged therein, does not cause changes in the packaging material that affect its integrity and functionality as a barrier to chemical or microbial contamination. Furthermore, "thermoresistant" is understood to mean that applying the same temperature and duration of heat to the packaging material as concurrently applied to the bulk mixed allergen material packaged therein, does not alter the packaging to cause a chemical in the packaging to be added to the bulk mixed allergen material packaged therein. For example, the thermoresistant packaging may include, but is not limited to, bulk bags, pouches, or stickpacks. In a further example, the thermoresistant packaging may be placed in boxes and/or on pallets or racks within a heating chamber for dry heat sterilization.

As contemplated in a described method of the present disclosure, blending may comprise loading 2 to 20 individual complete food allergens (e.g., 4 to 20, 6 to 20, 8 to 20, 10 to 20, 12 to 20, 14 to 20, 16 to 20, 18 to 20, 2 to 18, 4 to 18, 6 to 18, 8 to 18, 10 to 18, 12 to 18, 14 to 18, 16 to 18, 2 to 16, 4 to 16, 6 to 16, 8 to 16, 10 to 16, 12 to 16, or 14 to 16 individual complete food allergens) into a mechanical blender or mixer. For example, the mechanical blender or mixer may be selected from, but not limited to: a ribbon blender; a paddle blender; a plow blender; a fluidizing blender; an intensive mixer; a vacuum mixer; a conical mixer; a rotary batch mixer; and a double shaft mixer. In a particular embodiment, the individual complete food allergens are loaded into a ribbon blender. Without wishing to be bound by theory, it is believed that blending by loading the individual complete food allergens into a mechanical blender or mixer reduces grittiness, reduces the number of large particles, and increases homogeneity.

It will be appreciated that each individual complete food allergen may be loaded into the mechanical blender or mixer in various amounts including, for example, but not limited to: about 5 kg to about 100 kg; about 10 kg to about 90 kg; about 15 kg to about 80 kg; about 20 kg to about 70 kg; about 25 kg to about 60 kg; and about 30 kg to about 50 kg. It will be further appreciated that the mechanical blender or mixer may accommodate various total combined amounts of complete food allergens. In certain embodiments, for example, the mechanical blender or mixer may accommodate a total combined amount of complete food allergens of about 100 kg to about 2200 kg or about 500 kg to about 2000 kg. For example, in some embodiments the mechanical blender or mixer may accommodate an amount of about 500 kg, about 600 kg, about 700 kg, about 800 kg, about 900 kg, about 1000 kg, about 1100 kg, about 1200 kg, about 1500 kg, about 1600 kg, about 1700 kg, about 1800 kg, about 1900 kg, or about 2000 kg of total combined complete food allergens.

It will also be appreciated that the settings of the mechanical blender or mixer may be adjusted so as to achieve optimal blending and/or mixing of the individual complete food allergens. For example, the mechanical blender may be set to about 10 Hz to about 50 Hz (e.g., about 15 Hz to about 45 Hz, about 20 Hz to about 40 Hz, or about 25 Hz to about 35 Hz). The mechanical blender may also be set to operate for various lengths of time. For example, the mechanical blender may blend the individual food allergens for about 5 minutes to about 30 minutes, about 7.5 minutes to about 25 minutes, or about 10 minutes to about 20 minutes. In a particular embodiment, the mechanical blender or mixer is a 1000 kg capacity ribbon blender and blends the individual complete food allergens at 30 Hz for 15 minutes.

In certain embodiments, a method of the present disclosure further comprises blending the 2 to 20 individual complete food allergens with one or more than one bulking agents. Contemplated bulking agents may include any bulking agent described herein. In certain embodiments, the bulking agent comprises a sugar, for example, sucrose, maltodextrin, trehalose, trehalose dihydrate, isomalt, mannitol, lactose, dextrose, fructose, raffinose, or any combination thereof. In certain embodiments, the bulking agent comprises maltodextrin, or sucrose, or a combination thereof.

In certain embodiments, bulk mixed allergen material may be discharged from a mechanical blender or mixer into lined drums before being loaded for sterilization. In further embodiments, the bulk mixed allergen material discharged into lined drums may be packaged in bags or pouches.

Also contemplated is a method of making a mixed allergen product, further comprising filtering a mixed allergen product to remove agglomerate particles. For example, a mixed allergen product may be filtered through a screen ranging from a #5 mesh (US) screen to a #10 mesh (US) screen on a shaker for about 1 minute to about 10 minutes. For example, the screen may be a #5 mesh (US) screen, a #6 mesh (US) screen, a #7 mesh (US) screen, a #8 mesh (US) screen, a #9 mesh (US) screen, or a #10 mesh (US) screen. In a particular embodiment, the mixed allergen product is filtered through a screen ranging from a #5 mesh (US) screen to a #10 mesh (US) screen on a shaker for about 3 minutes.

In certain embodiments, a method of making a mixed allergen product may further comprise magnetically sifting a mixed allergen product to remove metallic particles. For example, magnetic sifting may comprise passing mixed allergen product through a rare earth magnet, a metal detector, and/or a metal separator. In a further example, the metal detector may detect stainless steel particles at least about 2 mm to about 2.5 mm in size, ferrous particles at least about 1.5 mm to about 2 mm in size, and non-ferrous particles with a sensitivity of about 1.5 to 2 parts per million.

In further embodiments, a method of making a mixed allergen product may be a continuous process, wherein the total completion time for the method is about 3 minutes to about 72 hours, about 30 minutes to about 72 hours, about 12 hours to about 72 hours, about 18 hours to about 72 hours, about 24 hours to about 72 hours, about 30 hours to about 72 hours, about 36 hours to about 72 hours, about 42 hours to about 72 hours, about 48 hours to about 72 hours, about 54 hours to about 72 hours, about 60 hours to about 72 hours, or about 66 hours to about 72 hours. For example, in particular examples, the total completion time for the method is about 30 minutes, about 45 minutes, about 60 minutes, about 75 minutes, about 90 minutes, about 105 minutes, about 120 minutes, about 12 hours, about 18 hours, about 24 hours, about 30 hours, about 36 hours, about 42 hours, about 48 hours, about 54 hours, about 60 hours, about 66 hours, or about 72 hours.

In methods of the present disclosure, sterilizing bulk mixed allergen material by dry heat sterilization, produces a mixed allergen product that is substantially free of replication viable organisms.

In certain embodiments, a mixed allergen product of the present disclosure is substantially free of replication viable bacteria, yeast, and/or molds. In some embodiments, a mixed allergen product may have: at least about a 1 log reduction to at least about a 9 log reduction; at least about a 1 log reduction to about a 4 log reduction; at least about a 1 log reduction to about a 5 log reduction; at least about a 1 log reduction to about a 6 log reduction; at least about a 1 log reduction to about a 7 log reduction; at least about a 1 log reduction to about a 8 log reduction, or at least about a 3 log reduction to about a 9 log reduction in aerobic bacterial organism plate counts as compared to a corresponding bulk mixed allergen material that has not been sterilized. For example, a mixed allergen product may have at least about a 1 log reduction, at least about a 2 log reduction, at least about a 3 log reduction, at least about a 4 log reduction, at least about a 5 log reduction, at least about a 6 log reduction, at least about a 7 log reduction, at least about a 8 log reduction, or at least about a 9 log reduction. in aerobic bacterial organism plate counts as compared to a corresponding bulk mixed allergen material that has not been sterilized. In a further example, a mixed allergen product has less than about 100,000 CFU/g, 10,000 CFU/g, less than about 1,000 CFU/g, less than about 100 CFU/g, or less than about 10 CFU/g of aerobic bacterial organisms. In another example, a mixed allergen product has less than about 100 CFU/g, less than about 10 CFU/g, or less than about 1 CFU/g of coliforms. In yet another example, a mixed allergen product may have less than about 10 CFU/g of a pathogenic microbial strain. For example, a mixed allergen product has less than about 100 CFU/g, less than about 10 CFU/g, or less than about 1 CFU/g of *Escherichia coli*. In a further example, a mixed allergen product has less than about 100 CFU/g, less than about 10 CFU/g, or less than about 1 CFU/g of *Enterobacteriaceae*. In another example, a mixed allergen product has less than about 100 CFU/g, or less than about 10 CFU/g of *Salmonella*. In another example, a mixed allergen product has less than about 100 CFU/g, or less than about 10 CFU/g of *Cronobacter*. In yet another example, a mixed allergen product is negative for *Listeria* species or *Cronobacter* species per 25 g sample of said mixed allergen product as determined by a PCR-based assay. In another example, a mixed allergen product has less than about 100 CFU/g, less than about 10 CFU/g, or less than about 1 CFU/g of mold. In yet another example, a mixed allergen product is negative for *Salmonella* species per 375 g sample of said mixed allergen product as determined by a PCR-based assay. In a further example, a mixed allergen product has less than about 100 CFU/g, less than about 10 CFU/g, or less than about 1 CFU/g of *Staphylococcus aureus*. In another example, a mixed allergen product has less than about 100 CFU/g, less than about 10 CFU/g, or less than about 1 CFU/g of yeast.

In certain embodiments, a mixed allergen product of the present disclosure has a fat content of at least about 5% by weight. For example, a mixed allergen product may have a fat content of about 10% to about 20% by weight. In some embodiments, for example, a mixed allergen product may have a fat content of about 10%, about 11%, about 12%, about 13%, about 14%, about 15%, about 16%, about 17%, about 18%, about 19%, or about 20% by weight.

It is contemplated that applying dry heat sterilization to bulk mixed allergen material will not substantially alter protein integrity. For example, in certain embodiments, a sterilized mixed allergen product has substantially the same protein integrity as a corresponding bulk mixed allergen material that has not been sterilized. In a further example, protein integrity is determined by SDS-PAGE, wherein mixed allergen product has substantially similar protein bands, protein band distribution, and protein band intensity as non-sterilized bulk mixed allergen material.

It is further contemplated that applying dry heat sterilization to bulk mixed allergen material will not substantially affect the ability of bulk mixed allergen material to elicit an allergen effect upon being consumed by an individual. As used herein, "allergen effect" is understood to mean an immune reaction to one or more than one antigenic component characterized by, but not limited to, immune cell activation, production of cytokines, and production of IgE. In certain embodiments, mixed allergen product has a substantially similar allergen effect upon being consumed by an individual as consumption of a substantially similar protein amount of corresponding bulk mixed allergen material that has not been sterilized. In certain embodiments, an allergen effect is measured by the production of IgE or cytokines, or measuring immune cell activation in response to consumption of bulk mixed allergen material or mixed allergen product by an individual. In other embodiments, the allergen effect is measured by an in vitro immune response, for example, measuring the production of IgE or cytokines, or measuring activation of immune cell cultures following treatment with bulk mixed allergen material or mixed allergen product.

In certain embodiments, a mixed allergen product of the present disclosure has a protein content of about 40% to about 50% by weight. For example, a mixed allergen product may have a protein content of about 40%, about 41%, about 42%, about 43%, about 44%, about 45%, about 46%, about 47%, about 48%, about 49%, or about 50% by weight.

In certain embodiments, a mixed allergen product of the present disclosure has about 1% to about 10% moisture by weight. For example, a mixed allergen product may have about 1%, about 2%, about 3%, about 4%, about 5%, about 6%, about 7%, about 8%, about 9%, or about 10% moisture by weight.

In certain embodiments, a mixed allergen product of the present disclosure has about 0.1 to about 0.6 water activity. "Water activity" is understood as the ratio between the vapor pressure of the mixed allergen product and the vapor pressure of distilled water under identical conditions. It will be appreciated that water activity is a measure of the water that is not bound to the molecules of the mixed allergen product and thus capable of supporting growth of bacteria, yeast and mold. Furthermore, it will be appreciated that water activity may be measured using suitable electronic instruments such as moisture meters, moisture-humidity meters, hygrometers, and relative humidity systems.

In certain embodiments, a mixed allergen product of the present disclosure has less than about 10% by weight of particles having a diameter greater than 500 μm.

In yet another embodiment, a mixed allergen product of the present disclosure has a substantially similar taste profile as compared to corresponding bulk mixed allergen material that has not been sterilized. For example, a mixed allergen product may have one or more than one flavor selected from, but not limited to, savory, nutty, marine, roasted, and brown. In a further example, a mixed allergen product does not have any off-flavors from processing.

In another embodiment, a method of making a mixed allergen product substantially free of replication viable organisms is contemplated, wherein 2 to 20 individual food allergens are sterilized by dry heat sterilization before blending to obtain a mixed allergen product.

In certain embodiments, a method of making a mixed allergen product further comprises blending the mixed allergen product with one or more than one probiotic selected from a group including, but not limited to, *Lactobacillus* species, *Bifidobacterium* species, *Anacaerostipes* species, and *Bacillus* species. For example, one or more probiotic may be selected from a group including, but not limited to *Lactobacillus rhamnosis, Anaerostipes caccae, Bifidobacterium longum, Bifidobacterium lactis, Lactobacillus plantarum, Lactobacillus acidophilus, Lactobacillus casei, Lactobacillus brevis, Lactobacillus salivarius, Lactococcus lactis, Bacillus coagulans, Lactobacillus bulgaricus, Lactobacillus gasseri, Lactobacillus paracasei, Bacillus coagulans* and *Bifidobacterium bifidum*. In a particular embodiment, a method of making a mixed allergen product further comprises blending the mixed allergen product with *Lactobacillus rhamnosis* and/or *Bifidobacterium longum*. As used herein, "probiotic" refers to a culture (pure or mixed), comprising microorganisms which, when ingested, beneficially affect the host.

In other embodiments, a method of making a mixed allergen product further comprises blending the mixed allergen product with one or more than one prebiotic selected from a group including, but not limited to, fructooligosaccharide, inulin, isomalto-oligosaccharide, lactilol, lactosucrose, lactulose, pyrodextrin, soybean oligosaccharide, xylooligosaccharide, transgalactooligosaccharide, oligosaccharide, soluble corn fiber, beta-glucan, oligofructose, and bipolymer. In a particular embodiment, a method of making a mixed allergen product further comprises blending the mixed allergen product with fructooligosaccharide. The term "prebiotic", as used herein, refers to a specific dietary food or nutrient that promotes the growth, proliferation, and/or activity of a specific, desirable, bacterial strain.

A disclosed mixed allergen product may further include one or more vitamins, as desired. Vitamins that may be present include, for example, vitamin A (e.g., in an amount ranging from about 1 to about 35,000 IU), vitamin C (e.g., in an amount ranging from about 1 to about 1,000 mg), vitamin D (e.g., in an amount ranging from about 1 to about 4,000 IU, i.e. from about 0.025 to about 100 mcg), vitamin E (e.g., in an amount ranging from about 1 to about 450 IU), vitamin K (e.g., in an amount ranging from about 1 to about 250 μg), vitamin B-1 (thiamin; e.g., in amount ranging from about 1 to about 15 mg), vitamin B-2 (riboflavin; e.g., in an amount ranging from about 1 to about 17 mg), vitamin B-3 (niacin; e.g., in an amount ranging from about 1 to about 200 mg), vitamin B-5 (pantothenic acid; e.g., in an amount ranging from about 1 to about 100 mg), vitamin B-6 (pyridoxine; e.g., in an amount ranging from about 1 to about 30 mg), vitamin B-9 (folic acid; e.g., in an amount ranging from about 1 to about 4,000 μg), vitamin B-12 (cobalamin; e.g., in an amount ranging from about 1 to about 250 μg), vitamin H (biotin; e.g., in an amount ranging from about 1 to about 1,000 μg) and combinations thereof. In certain embodiments, a mixed allergen product comprises vitamin D. In certain embodiments, a mixed allergen product comprises 400 IU, i.e. about 10 μg, of vitamin D.

Also contemplated is a method of making a mixed allergen product, wherein the mixed allergen product is further mixed with a physiologically acceptable delivery vehicle to produce a physiologically acceptable composition. Mixed allergen products can be further incorporated into a variety of formulations for administration to a subject. More particularly, a mixed allergen product can be formulated into a physiological acceptable composition by combination with appropriate, physiologically acceptable carriers or diluents, for example, a vegetable oil.

In certain embodiments, a disclosed mixed allergen product is designed for oral immunotherapeutic treatment of food allergy in a child or adult, for example, as dispersible powders or granules, foods, tablets, troches, lozenges, gummies, emulsions, etc. Compositions intended for oral use may be prepared according to any convenient protocol for the manufacture of oral compositions and such compositions may contain one or more agents selected from the group consisting of sweetening agents (e.g., glycerol, propylene glycol, sorbitol, or sucrose), flavoring agents, coloring agents and preserving agents in order to provide palatable preparations.

Also contemplated is a method of making a mixed allergen product, wherein the mixed allergen product is mixed or incorporated with food to which a child or adult is not allergic. For example, foods may include, but are not limited to: baby or infant formula, baby food (e.g., pureed food suitable for infant or toddler consumption), chips, cookies, breads, spreads, creams, yogurts, liquid drinks, chocolate containing products, candies, ice creams, cereals, coffees, pureed food products, etc.

Throughout the description, where apparatus, devices, and systems are described as having, including, or comprising specific components, or where processes and methods are described as having, including, or comprising specific steps, it is contemplated that, additionally, there are apparatus, devices, and systems that consists essentially of, or consist of, the recited components, and that there are processes and methods that consist essentially of, or consist of, the recited processing steps.

All examples presented herein are for illustrative purposes only, and should not be construed as limiting in any way.

EXAMPLES

Example 1

This example describes the selection of allergenic food ingredients for inclusion in an exemplary dry powder mixed allergen product containing 16 individual complete food allergens (almond, cashew, hazelnut, peanut, pecan, pistachio, walnut, sesame, soy, egg, milk, oat, wheat, cod, salmon, and shrimp).

Ingredients were sourced with primary emphasis on domestic commercial availability, with exceptions made for individual complete food allergens that were only available internationally. Successful commercial sourcing of multiple options per each individual complete food allergen led to development of selection criteria in order to choose the best commercial food allergen to be tested. Attributes screened included: protein content; bulking material content; organoleptic attributes such as taste, presence of off-notes, and grittiness; and solubility. Ingredients having considerably low protein content, or having a large proportion of bulking materials were eliminated from contention. Individual complete food allergens were tasted dry to determine the presence of off-flavors and to assess grittiness.

TABLE 1 shows a sample formulation for a mixed allergen product and representative pre-weighed batch amounts of individual complete food allergens provided for blending and sterilization.

TABLE 1

| Individual Complete Food Allergen | Formulation (g) | Formulation (%) | Batch for Sterilization Run (kg) | Actual Batch (kg) |
|---|---|---|---|---|
| Almond Powder, 50% | 0.6895 | 6.620 | 33.10 | 33.10 |
| Cashew Powder, 35% | 0.10720 | 10.294 | 51.47 | 51.47 |
| Cod Powder | 0.02291 | 2.200 | 11.00 | 11.00 |
| Whole Egg Powder | 0.06742 | 6.473 | 32.37 | 32.37 |
| Hazelnut Powder | 0.08824 | 8.472 | 42.36 | 42.36 |
| Milk Protein Isolate | 0.03534 | 3.393 | 16.96 | 6.35 |
| Oat Protein | 0.06266 | 6.017 | 30.08 | 30.08 |
| Peanut Powder | 0.06122 | 5.879 | 29.39 | 29.39 |
| Pecan Powder | 0.09816 | 9.425 | 47.13 | 47.13 |
| Pistachio Powder | 0.08867 | 8.514 | 42.57 | 42.57 |
| Salmon Protein Powder | 0.07560 | 7.259 | 36.30 | 36.30 |
| Sesame Seed Powder | 0.06100 | 5.857 | 29.28 | 29.28 |
| Shrimp Powder | 0.04261 | 4.092 | 20.46 | 20.46 |
| Soy Protein Isolate | 0.03736 | 3.588 | 17.94 | 17.94 |
| Walnut Powder | 0.08316 | 7.985 | 39.93 | 39.93 |
| Wheat Gluten | 0.04096 | 3.933 | 19.67 | 19.67 |
| Total | 1.04146 | 100.00 | 500.00 | 489.39 |

Example 2

This example describes an exemplary blending process for the preparation of a mixed allergen product comprising 16 individual complete food allergens (almond, cashew, hazelnut, peanut, pecan, pistachio, walnut, sesame, soy, egg, milk, oat, wheat, cod, salmon, and shrimp).

A 1,000 kg ribbon blender (Prince Industries, India) was cleaned, sanitized, and tested for adenosine triphosphate (ATP) and allergens. Actual batch amounts (in kg) of 16 individual complete food allergens as indicated in Table 1 were loaded into the ribbon blender and blended at 30 Hz for 15 minutes.

Bulk mixed allergen material was discharged from the ribbon blender into lined drums (40 to 50 kg per drum).

Example 3

This example describes an alternative blending and milling process for the preparation of a mixed allergen product comprising 16 individual complete food allergens (almond, cashew, hazelnut, peanut, pecan, pistachio, walnut, sesame, soy, egg, milk, oat, wheat, cod, salmon, and shrimp).

All individual complete food allergens were weighed to make 8 kg batches. Individual complete food allergens were transferred to a D500 Hobart mixer equipped with a D-30 Bowl and safety cage. Individual complete food allergens were mixed with a paddle attachment "B" flat beater on setting 1 for 2 minutes. Blended complete food allergens were transferred to large, food-grade, plastic bags, sealed, and stored at room temperature until milling. Blended complete food allergens were slowly fed into a Quadro SLS-L1A FitzMill equipped with a #20 mesh screen and set to 9,000 rpm to achieve a target particle size of <500 µm in diameter. Milled complete food allergens were passed through a metal detector and #35 mesh screen before packaging.

Example 4

A preliminary test for heat sensitivity was conducted to determine the suitability of the bulk mixed allergen material for sterilization treatment.

Bulk mixed allergen material was placed in a pan and subjected to different temperatures in a laboratory oven for 5 minutes.

As shown in FIG. 1, apart from a slight darkening in color with increased temperature, bulk mixed allergen material did not exhibit any other physical alterations with heat treatments of 95° C., 105° C., 110° C., or 120° C. for 5 minutes that would make the material unsuitable for sterilization treatment.

Example 5

This example describes an exemplary dry heat sterilization process that can be used for the preparation of a mixed allergen product comprising 16 individual food allergens (almond, cashew, hazelnut, peanut, pecan, pistachio, walnut, sesame, soy, egg, milk, oat, wheat, cod, salmon, and shrimp). A dry heat sterilization method similar to that which is contemplated in the present disclosure is described in US 2014/0023757, which is herein incorporated by reference.

Bulk mixed allergen material, blended as described in Examples 2 or 3, can be bagged in thermoresistant packaging. The bagged bulk mixed allergen material can then be placed in an insulated heat treatment chamber, wherein heat is supplied to the treatment chamber by multiple natural gas fired furnaces. Heat can be circulated through the insulated treatment chamber using multiple intake and exhaust ducts to facilitate uniform absorption of heat by the bagged bulk mixed allergen material.

For example, 6 bags of bulk mixed allergen material, each weighing about 25 lbs./12 kg can be placed as a single layer on a pallet, and 14 pallets can be loaded into a heating chamber having dimensions of 40 feet long, 10 feet high, and 9 feet wide.

The heating chamber can then be sealed, and the chamber can be heated to reach the target temperature of 74° C. Warm-up time for the chamber to reach the target temperature may take up to about 24 hours.

The temperature of the heating chamber can be monitored using six probes within the heating chamber. For example, two probes may be placed in the back of the heating chamber, two probes may be place in the middle of the heating chamber, and two probes may be placed at the front of the heating chamber.

Once the target temperature is reached, the heating chamber can be maintained for a period of 24 hours.

Temperatures of the insulated treatment chamber, multiple natural gas fired furnaces, and bagged bulk mixed allergen material can be monitored to ensure that the bulk mixed allergen material is applied with dry heat sterilization at a temperature of about 65° C. to about 175° C. for a period of 24 hours.

Following dry heat treatment, the sterilized mixed allergen product can be unloaded from the heating chamber. Water activity, moisture level, and total plate counts can be measured for samples of the sterilized mixed allergen product and compared to samples of the bulk mixed allergen material prior to dry heat sterilization.

For example, samples can be diluted and spread onto petri dishes of general recovery media to measure colony-forming units per gram of product or material (CFU/g) for total aerobic microorganism and *Enterobacteriaceae* counts. *E. coli*/coliform, and *S. aureus* counts can be determined by diluting samples and spreading onto 3M Petrifilm™ *E. coli*/coliform and 3M Petrifilm™ Staph Express count plates, respectively, in accordance with the manufacturer's instructions (3M, St. Paul, Minn.).

Samples can be additionally tested for the presence of *Listeria* and *Salmonella* using the BAX® PCR detection system (Hygiena, Camarillo, Calif.) in accordance with the manufacturer's instructions.

Total mold and yeast counts can also be determined by diluting samples and spreading onto 3M Petrifilm™ mold and yeast count plates in accordance with the manufacturer's instructions.

Example 6

This example describes the validation of a dry heat process for sterilization of bulk mixed allergen material.

In this dry heat process, SurroNov® 1830, a strain derived from *Enterococcus Faecium* ATCC® 8459, was used as a surrogate microorganism to evaluate the lethality of the dry heat sterilization on *Salmonella* and *Cronobacter* pathogens. SurroNov® 1830 has a thermal resistance similar to, or greater than, the thermal resistance of *Salmonella* and *Cronobacter*. Validation was aimed at achieving at least a 5-log reduction in the number of viable SurroNov® 1830 organisms. Two validation trials were performed to evaluate variability.

Before dry heat sterilization, 70 thermoresistant bags, each containing 25 g of bulk mixed allergen material blended as described in Examples 2 or 3, were inoculated with approximately $1.4 \times 10^6$ SurroNov® 1830 organisms. Each inoculated thermoresistant bag was placed into a box.

Six inoculated bags of bulk mixed allergen material were not introduced into the dry heat sterilization process and served as non-treated control samples.

Figure 2A:
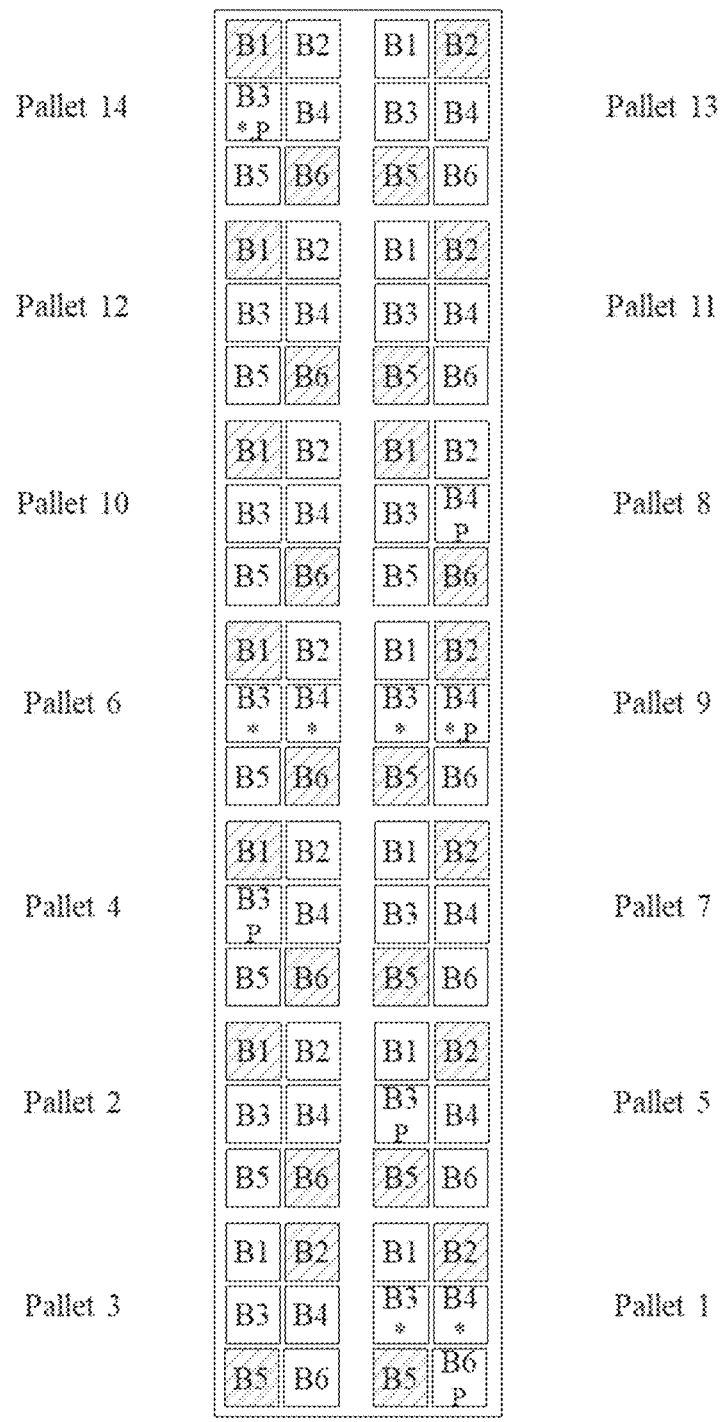
FIG. 2A is a schematic showing the placement of pallets and sample boxes containing thermoresistant bags of bulk mixed allergen material in a dry heat sterilization chamber for validation trial 1. B3 of pallets 3, 4 and 12 have chamber probes placed inside the boxes for temperature monitoring. B4 of pallets 7 and 8 have chamber probes placed outside the boxes, and B4 of pallet 11 has a chamber probe placed inside the box.

14 pallets, each containing four boxes of inoculated thermoresistant bags of bulk mixed allergen material, were loaded into the heating chamber as shown in FIGS. 2A and 2B for validation trials 1 and 2, respectively. On pallets 1, 6, 9, and 14, second inoculated thermoresistant bags of bulk mixed allergen material were placed into boxes 3 and/or 4.

Temperature of the heating chamber was monitored throughout the validation run using heat chamber probes: two positioned at the front of the heating chamber, two positioned in the middle of the heating chamber, and two positioned at the back of the heating chamber. Additionally, MadgeTech probes were included to monitor temperature of the heating chamber during the dry heat sterilization process. MadgeTech probes were either placed inside select inoculated thermoresistant bags of bulk mixed allergen material or outside the boxes.

Figure 3A:
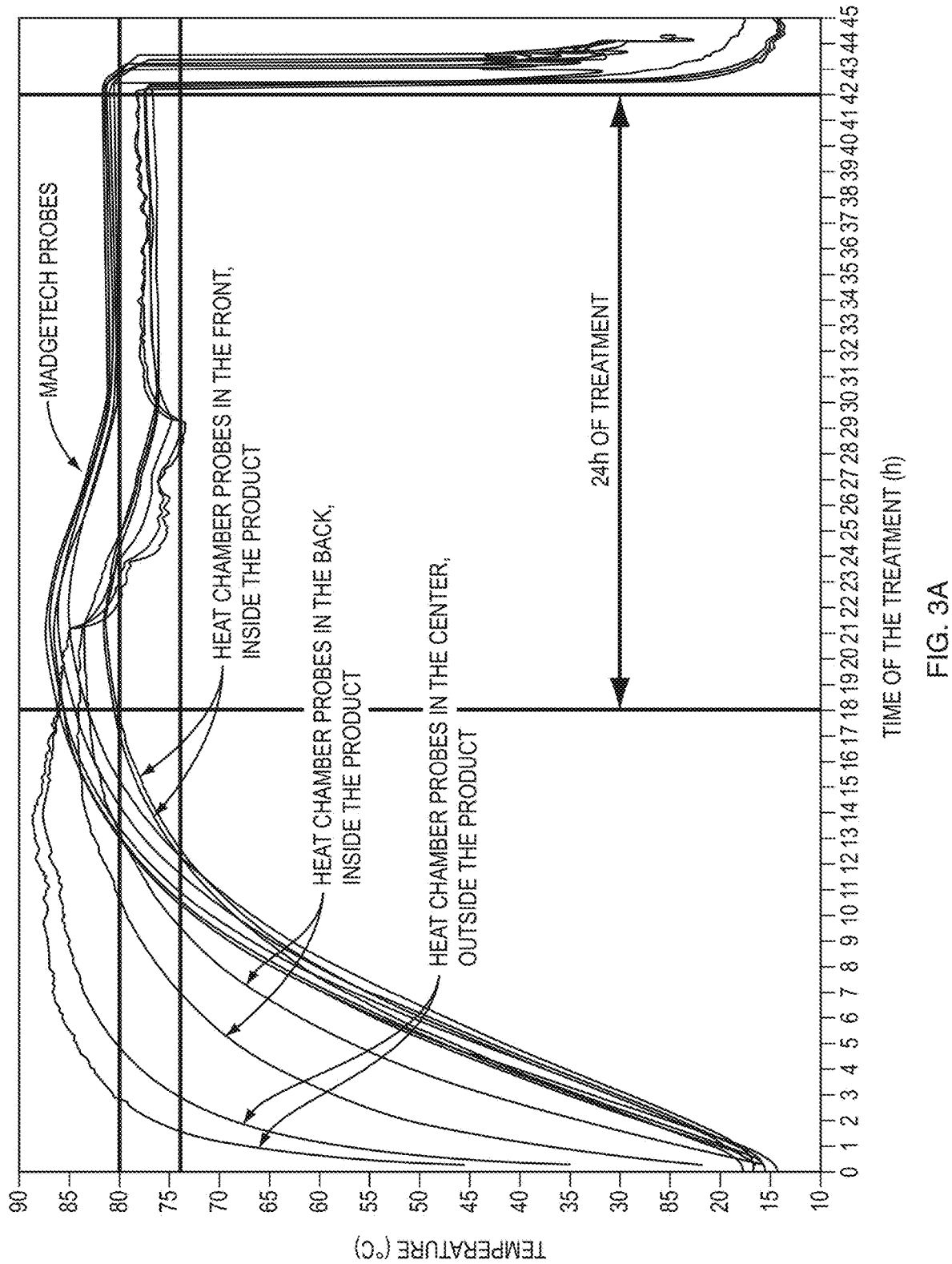
FIG. 3A is line graph showing the temperature profile of the dry heat sterilization chamber during validation trial 1.
Figure 3B:
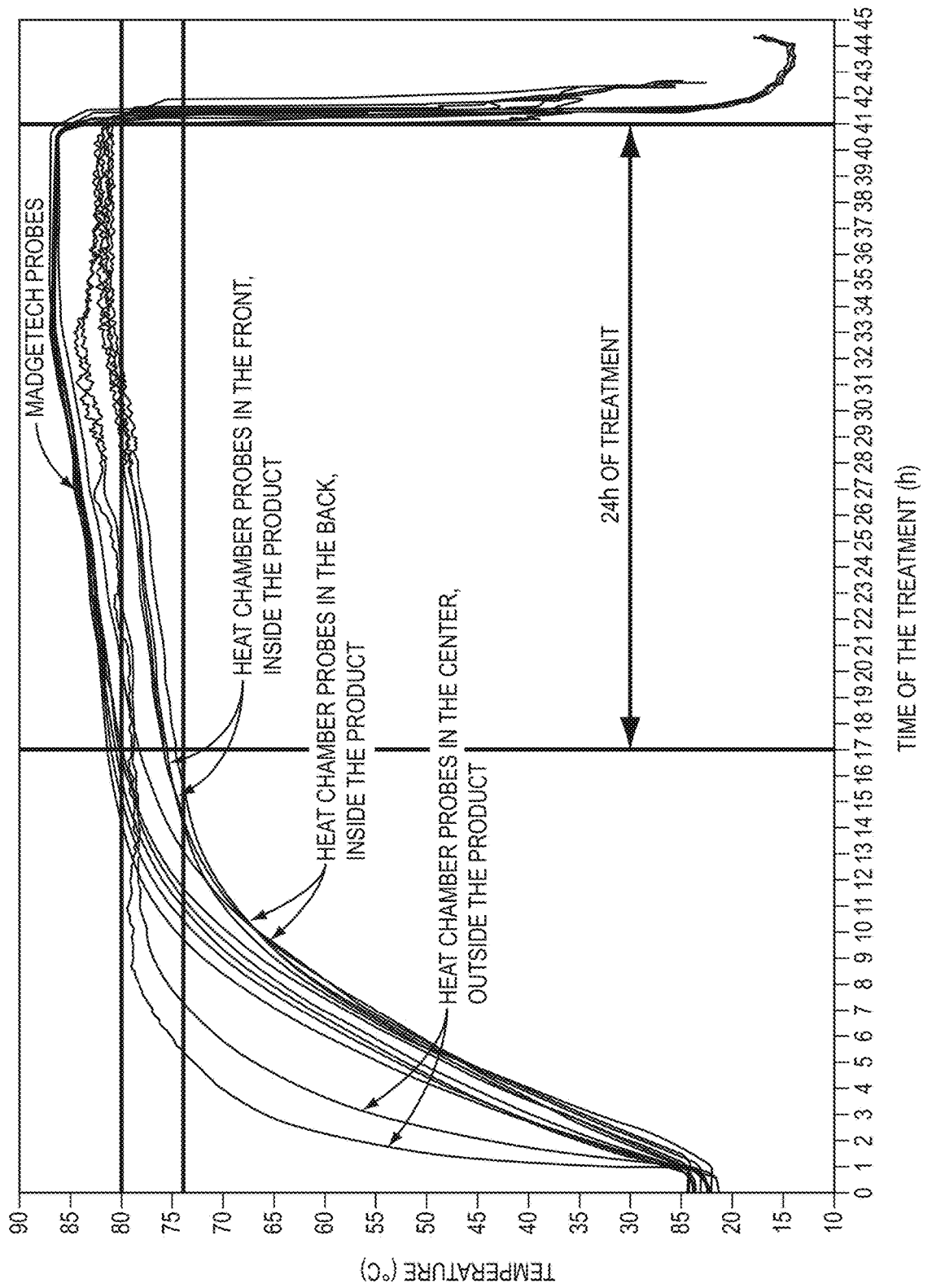
FIG. 3B is line graph showing the temperature profile of the dry heat sterilization chamber during validation trial 2. Each line represents the temperature readings of a single chamber probe or MadgeTech probe.

As shown in FIGS. 3A and 3B for validation trials 1 and 2, respectively, the temperature recorded by the MadgeTech probes are relatively homogeneous at different positions inside the chamber. Temperatures recorded by the heat chamber probes differ depending on the position inside the chamber (i.e. back, middle, or front), but temperatures between two probes in the same position are relatively similar during the dry heat sterilization treatment.

For validation trial 1 (FIG. 3A), the dry heat treatment was initially set to 175° F./80° C. It took 18 hours for all probes to reach the target temperature. Once the target temperature was attained, the temperature was decreased to 165° F./74° F. and maintained at this temperature for an additional 24 hours.

For validation trial 2 (FIG. 3B), the dry heat treatment was set to 165° F./74° C. It took 17 hours for all probes to reach the target temperature. Once the target temperature was attained, the dry heat sterilization temperature was maintained at 165° F./74° C. for an additional 24 hours.

As shown in TABLE 2, water activity and moisture content of sterilized mixed allergen product after validation trial 1 dry heat sterilization is lower than the water activity and moisture content of bulk mixed allergen material before dry heat treatment. Total plate counts on selective media were similar for bulk mixed allergen material before dry heat sterilization and mixed allergen product after dry heat sterilization.

TABLE 2

| | Water Activity ($a_w$) | Moisture Content (%) | Log Total Plate Count |
|---|---|---|---|
| Bulk Mixed Allergen Material (before dry heat sterilization) | 0.286 ± 0.002 | 1.63 ± 0.08% | 3.0 ± 0.3 log cfu/g |
| Mixed Allergen Product (after dry heat sterilization) | 0.235 ± 0.029 | 1.26 ± 0.21% | 2.8 ± 0.7 log cfu/g |

As shown in TABLE 3, bulk mixed allergen material samples that were not treated with dry heat sterilization had a mean SurroNov® 1830 count of 8.1±0.1 log cfu/g.

TABLE 3

| Control Sample | CFU/g | Log | Mean |
|---|---|---|---|
| 1 | $1.4 \times 10^8$ | 8.1 | 8.1 ± 0.1 |
| 2 | $1.5 \times 10^8$ | 8.2 | |
| 3 | $1.5 \times 10^8$ | 8.2 | |
| 4 | $1.2 \times 10^8$ | 8.1 | |
| 5 | $1.3 \times 10^8$ | 8.1 | |
| 6 | $1.5 \times 10^8$ | 8.2 | |

As shown in TABLE 4, greater than 5 log reductions in SurroNov® 1830 CFU/g was achieved in all samples following dry heat sterilization in validation trial 1, as compared to inoculated bulk mixed allergen material samples that were not dry heat treated.

TABLE 4

| ID | CFU/g | Log | Log Reduction |
|---|---|---|---|
| PS7 | <10 | <1 | >7.1 |
| PS8 | <10 | <1 | >7.1 |
| PS9 | <10 | <1 | >7.1 |
| PS10 | <10 | <1 | >7.1 |
| PS11 | <10 | <1 | >7.1 |
| PS12 | <10 | <1 | >7.1 |
| PS13 | <10 | <1 | >7.1 |
| PS14 | <10 | <1 | >7.1 |
| PS15 | <10 | <1 | >7.1 |
| PS16 | <10 | <1 | >7.1 |
| PS17 | <10 | <1 | >7.1 |
| PS18 | <10 | <1 | >7.1 |
| PS19 | <10 | <1 | >7.1 |
| PS20 | <10 | <1 | >7.1 |
| PS21 | <10 | <1 | >7.1 |
| PS22 | <10 | <1 | >7.1 |
| PS23 | <10 | <1 | >7.1 |
| PS24 | <10 | <1 | >7.1 |
| PS25 | <10 | <1 | >7.1 |
| PS26 | <10 | <1 | >7.1 |
| PS27 | <10 | <1 | >7.1 |
| PS28 | <10 | <1 | >7.1 |
| PS29 | <10 | <1 | >7.1 |
| PS30 | <10 | <1 | >7.1 |
| PS31 | <10 | <1 | >7.1 |
| PS32 | <10 | <1 | >7.1 |
| PS33 | <10 | <1 | >7.1 |
| PS34 | <10 | <1 | >7.1 |
| PS35 | <10 | <1 | >7.1 |
| PS36 | <10 | <1 | >7.1 |
| PS37 | <10 | <1 | >7.1 |
| PS38 | <10 | <1 | >7.1 |
| PS39 | <10 | <1 | >7.1 |
| PS40 | <10 | <1 | >7.1 |
| PS41 | <10 | <1 | >7.1 |
| PS42 | <10 | <1 | >7.1 |
| PS43 | <10 | <1 | >7.1 |
| PS44 | <10 | <1 | >7.1 |
| PS45 | <10 | <1 | >7.1 |
| PS46 | <10 | <1 | >7.1 |
| PS47 | <10 | <1 | >7.1 |
| PS48 | <10 | <1 | >7.1 |
| PS49 | 410 | 2.6 | 5.5 |
| PS50 | 20 | 1.3 | 6.8 |
| PS51 | <10 | <1 | >7.1 |
| PS52 | <10 | <1 | >7.1 |
| PS53 | <10 | <1 | >7.1 |
| PS54 | <10 | <1 | >7.1 |
| PS55 | <10 | <1 | >7.1 |
| PS56 | 10 | 1 | 7.1 |
| PS57 | <10 | <1 | >7.1 |
| PS58 | <10 | <1 | >7.1 |
| PS59 | <10 | <1 | >7.1 |
| PS60 | <10 | <1 | >7.1 |
| PS61 | <10 | <1 | >7.1 |
| PS62 | <10 | <1 | >7.1 |
| PS63 | <10 | <1 | >7.1 |
| PS64 | <10 | <1 | >7.1 |
| PS65 | <10 | <1 | >7.1 |

TABLE 4-continued

| ID | CFU/g | Log | Log Reduction |
| --- | --- | --- | --- |
| PS66 | <10 | <1 | >7.1 |
| PS67 | <10 | <1 | >7.1 |
| PS68 | <10 | <1 | >7.1 |
| PS69 | <10 | <1 | >7.1 |
| PS70 | <10 | <1 | >7.1 |

As shown in TABLE 5, water activity of sterilized mixed allergen product after validation trial 2 dry heat sterilization is similar to the water activity of bulk mixed allergen material before dry heat treatment. Moisture content and total plate counts were lower following dry heat sterilization treatment in validation trial 2, as compared to bulk mixed allergen material that was not dry heat sterilized.

TABLE 5

| | Water Activity ($a_w$) | Moisture Content (%) | Log Total Plate Count |
| --- | --- | --- | --- |
| Bulk Mixed Allergen Material (before dry heat sterilization) | 0.285 ± 0.005 | 1.95 ± 0.10% | 3.0 ± 0.3 log cfu/g |
| Mixed Allergen Product (after dry heat sterilization) | 0.301 ± 0.054 | 1.22 ± 0.12% | 2.5 ± 0.1 log cfu/g |

As shown in TABLE 6, bulk mixed allergen material samples that were not treated with dry heat sterilization had a mean SurroNov® 1830 count of 8.1±0.1 log cfu/g.

TABLE 6

| Control Sample | CFU/g | Log | Mean |
| --- | --- | --- | --- |
| 1 | $1.5 \times 10^8$ | 8.2 | 8.1 ± 0.1 |
| 2 | $1.3 \times 10^8$ | 8.1 | |
| 3 | $1.1 \times 10^8$ | 8.0 | |
| 4 | $1.1 \times 10^8$ | 8.0 | |
| 5 | $6.9 \times 10^7$ | 7.8 | |
| 6 | $1.3 \times 10^8$ | 8.1 | |
| 7 | $1.1 \times 10^8$ | 8.0 | |
| 8 | $1.4 \times 10^8$ | 8.1 | |

Similarly to dry heat sterilization in validation trial 1, as shown in TABLE 7, dry heat sterilization in validation trial 2 resulted in greater than 5 log reductions in SurroNov® 1830 CFU/g in all samples, as compared to inoculated bulk mixed allergen material samples that were not dry heat treated.

TABLE 7

| ID | CFU/g | Log | Log Reduction |
|---|---|---|---|
| PS7 | <10 | <1 | >7.1 |
| PS8 | <10 | <1 | >7.1 |
| PS9 | <10 | <1 | >7.1 |
| PS10 | <10 | <1 | >7.1 |
| PS11 | <10 | <1 | >7.1 |
| PS12 | <10 | <1 | >7.1 |
| PS13 | <10 | <1 | >7.1 |
| PS14 | <10 | <1 | >7.1 |
| PS15 | <10 | <1 | >7.1 |
| PS16 | <10 | <1 | >7.1 |
| PS17 | <10 | <1 | >7.1 |
| PS18 | <10 | <1 | >7.1 |
| PS19 | <10 | <1 | >7.1 |
| PS20 | <10 | <1 | >7.1 |
| PS21 | <10 | <1 | >7.1 |

TABLE 7-continued

| ID | CFU/g | Log | Log Reduction |
|---|---|---|---|
| PS22 | <10 | <1 | >7.1 |
| PS23 | <10 | <1 | >7.1 |
| PS24 | <10 | <1 | >7.1 |
| PS25 | <10 | <1 | >7.1 |
| PS26 | 20 | 1.3 | 6.8 |
| PS27 | <10 | <1 | >7.1 |
| PS28 | <10 | <1 | >7.1 |
| PS29 | <10 | <1 | >7.1 |
| PS30 | <10 | <1 | >7.1 |
| PS31 | <10 | <1 | >7.1 |
| PS32 | <10 | <1 | >7.1 |
| PS33 | <10 | <1 | >7.1 |
| PS34 | <10 | <1 | >7.1 |
| PS35 | <10 | <1 | >7.1 |
| PS36 | <10 | <1 | >7.1 |
| PS37 | 20 | 1.3 | 6.8 |
| PS38 | <10 | <1 | >7.1 |
| PS39 | <10 | <1 | >7.1 |
| PS40 | <10 | <1 | >7.1 |
| PS41 | <10 | <1 | >7.1 |
| PS42 | <10 | <1 | >7.1 |
| PS43 | <10 | <1 | >7.1 |
| PS44 | <10 | <1 | >7.1 |
| PS45 | <10 | <1 | >7.1 |
| PS46 | <10 | <1 | >7.1 |
| PS47 | <10 | <1 | >7.1 |
| PS48 | <10 | <1 | >7.1 |
| PS49 | 410 | 2.6 | 5.5 |
| PS50 | 20 | 1.3 | 6.8 |
| PS51 | <10 | <1 | >7.1 |
| PS52 | <10 | <1 | >7.1 |
| PS53 | <10 | <1 | >7.1 |
| PS54 | <10 | <1 | >7.1 |
| PS55 | <10 | <1 | >7.1 |
| PS56 | 10 | 1 | 7.1 |
| PS57 | <10 | <1 | >7.1 |
| PS58 | <10 | <1 | >7.1 |
| PS59 | <10 | <1 | >7.1 |
| PS60 | <10 | <1 | >7.1 |
| PS61 | <10 | <1 | >7.1 |
| PS62 | <10 | <1 | >7.1 |
| PS63 | <10 | <1 | >7.1 |
| PS64 | <10 | <1 | >7.1 |
| PS65 | <10 | <1 | >7.1 |
| PS66 | <10 | <1 | >7.1 |
| PS67 | <10 | <1 | >7.1 |
| PS68 | <10 | <1 | >7.1 |
| PS69 | <10 | <1 | >7.1 |
| PS70 | <10 | <1 | >7.1 |

Example 7

Particle size distribution can be measured for mixed allergen product samples treated with dry heat sterilization and compared to the particles of corresponding bulk mixed allergen material that did not receive application of dry heat sterilization. Samples can be filtered for 3 minutes using a Ro-Tap® sieve shaker and a series of mesh sizes consisting of: #10, #12, #14, #16, #18, #20, #25, #30, #35, #40, and #50 meshes. Filtered particles and particles retained by each mesh can be individually removed, weighed, and distributions plotted as % weight versus particle size (in μm).

Example 8

Protein integrity of mixed allergen product samples treated with dry heat sterilization can be compared to bulk mixed allergen material that did not receive application of dry heat sterilization. Protein integrity can be assessed by resolving all proteins present in non-sterilized and dry heat-sterilized samples by SDS-PAGE.

1 mg of bulk mixed allergen material or dry heat sterilized mixed allergen product can be weighed into 2 mL microtubes. Based on their assessed protein concentrations, samples can be diluted with Laemmli buffer containing 5% 2-mercaptoethanol (BioRad, Hercules, Calif.) to a protein concentration of 1 mg/ml. Protein suspensions can be mixed by gentle inversion or intermittent vortexing for 5 minutes then heated to 95° C. to 100° C. for 5 minutes. Samples can be centrifuged for 1 minute at 1,000 RPM, then 10 μl of each sample can be loaded per well, in triplicate, on a 4-20% polyacrylamide gradient gel (BioRad, Hercules, Calif.) immersed in 1×SDS-PAGE running buffer (BioRad, Hercules, Calif.). Gels can be run at 100 V for 80-90 minutes (or 200V for 30-40 minutes). Gels can then be washed 3 times with distilled water, 5 minutes per wash, on an orbital shaker at room temperature. Gels can be fixed in fixing solution (Sigma-Aldrich, St. Louis, Mo.) or 50% methanol, 10% acetic acid, for 15 minutes. Gels can be stained with EX Blue gel staining reagent (Sigma-Aldrich, St. Louis, Mo.) for 2 hours or overnight, then de-stained by washing in distilled water for 1-2 hours or overnight. Upon completion of washing, gels can be covered with clear plastic and scanned using a gel reader. Protein band densitometry can be analyzed using ImageJ public domain software (NIH, Bethesda, Md.).

Example 9

The visual and organoleptic characteristics of mixed allergen product samples treated with dry heat sterilization can be compared to bulk mixed allergen material that did not receive application of dry heat sterilization. A comparison of taste profiles of dry heat sterilized mixed allergen product and non-sterilized bulk mixed allergen can also be performed.

INCORPORATION BY REFERENCE

All publications and patents mentioned herein are hereby incorporated by reference in their entirety for all purposes. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method of making a mixed allergen product substantially free of replication viable organisms, comprising:

blending 2 to 20 individual complete food allergens together to obtain bulk mixed allergen material comprising the 2 to 20 individual complete food allergens, wherein the blending comprises loading the 2 to 20 individual complete food allergens into a ribbon blender set at about 10 Hz to about 50 Hz for about 10 minutes to about 50 minutes; and sterilizing the bulk mixed allergen material by dry heat sterilization, thereby obtaining the mixed allergen product.

2. The method of claim 1, wherein the individual complete food allergens are selected from the group consisting of almond, cashew, cod, egg, hazelnut, milk, oat, peanut, pecan, pistachio, salmon, sesame, shrimp, soy, walnut, and wheat.

3. The method of claim 1, wherein the blending further comprises blending the 2 to 20 individual complete food allergens with at least one bulking agent.

4. The method of claim 1, wherein the dry heat sterilization is at a temperature of about 65° C. to about 175° C. for about 18 hours to about 72 hours.

5. The method of claim 4, wherein the dry heat sterilization comprises using a sterilization system having a furnace and a heating chamber, wherein the furnace provides about 250,000 BTUs to about 750,000 BTUs of heat to the heating chamber.

6. The method of claim 4, wherein the bulk mixed allergen material is packaged into thermoresistant packaging before the sterilizing.

7. The method of claim 1, wherein the mixed allergen product has at least about a 1 log reduction in aerobic bacterial organism plate counts as compared to corresponding bulk mixed allergen material that has not been sterilized.

8. The method of claim 1, wherein the mixed allergen product has less than about 100,000 CFU/g of aerobic bacterial organisms.

9. The method of claim 1, wherein the mixed allergen product has less than about 10 CFU/g of coliforms, less than about 10 CFU/g of *Escherichia coli*, less than about 10 CFU/g of Enterobacteriaceae, less than about 10 CFU/g of *Salmonella*, less than about 10 CFU/g of *Cronobacter*, less than about 10 CFU/g of mold, less than about 10 CFU/g of *Staphylococcus aureus*, and/or less than about 10 CFU/g of yeast.

10. The method of claim 1, wherein the mixed allergen product is negative in a PCR-based assay for *Listeria* species or *Cronobacter* species per 25 grams of the mixed allergen product, or for *Salmonella* species per 375 g of the mixed allergen product.

11. The method of claim 1, wherein protein integrity of the mixed allergen product is substantially similar to protein integrity of corresponding bulk mixed allergen material that has not been sterilized.

12. The method of claim 1, wherein the mixed allergen product has a protein content of about 40% to about 50% by weight.

13. The method of claim 1, wherein the mixed allergen product has about 1% to about 10% moisture by weight.

14. The method of claim 1, wherein the mixed allergen product has a water activity of about 0.1 to about 0.6.

15. The method of claim 1, wherein less than about 10% by weight of the mixed allergen product are particles having a diameter greater than 500 μm.

16. The method of claim 1, wherein the mixed allergen product has a substantially similar taste profile as compared to corresponding bulk mixed allergen material that has not been sterilized.

17. The method of claim 1, wherein the sterilizing further comprises at least one additional application of dry heat sterilization.

18. A method of making a mixed allergen product substantially free of replication viable organisms, comprising:

blending 2 to 20 individual complete food allergens in a mechanical mixer to obtain bulk mixed allergen material;

milling the bulk mixed allergen material to obtain milled mixed allergen material having less than about 10% by weight of particles having a diameter greater than 500 µm;

filtering the milled mixed allergen material to remove the particles having a diameter greater than 500 µm, to obtain a filtered mixed allergen material; and sterilizing the filtered mixed allergen material, which comprises the 2 to 20 individual complete food allergens, by dry heat sterilization, thereby obtaining the mixed allergen product.

19. The method of claim 1, further comprising blending the mixed allergen product with at least one probiotic selected from the group consisting of *Lactobacillus rhamnosus, Anaerostipes caccae*, and *Bifidobacterium longum.*

20. The method of claim 1, further comprising blending the mixed allergen product with at least one prebiotic.

21. The method of claim 20, wherein the at least one prebiotic comprises fructooligosaccharide.

22. The method of claim 1, further comprising filtering the mixed allergen product through a screen ranging from a #5 mesh (US) screen to a #10 mesh (US) screen on a shaker for about 1 minute to about 10 minutes.

23. The method of claim 1, further comprising passing the mixed allergen product through a rare earth magnet, metal detector, and metal separator.

* * * * *